United States Patent
Smith et al.

(10) Patent No.: US 6,444,846 B1
(45) Date of Patent: Sep. 3, 2002

(54) PROCESS FOR PREPARING TETRAFLUOROBORATE SALT AND INTERMEDIATES THEREOF

(75) Inventors: W. Novis Smith; Joel McCloskey, both of Philadelphia, PA (US)

(73) Assignee: Lithdyn International, Anaheim, CA (US)

( * ) Notice: Subject to any disclaimer, the term of this patent is extended or adjusted under 35 U.S.C. 154(b) by 0 days.

(21) Appl. No.: 09/838,479

(22) Filed: Apr. 19, 2001

(51) Int. Cl.$^7$ .................................................. C07F 5/02
(52) U.S. Cl. ........................................... 564/8; 564/296
(58) Field of Search ....................................... 564/8, 296

(56) References Cited

PUBLICATIONS

CA:123:46674 abs Inorg Chem by Pacheco et al 34(13) pp. 3477–3484 1995.*
CA:132:93030 abs JP2000026473 Jan. 2000.*
CA:96:21931 abs Mater. Ogolnopol. Symp. Zwiazki Flourowych by Zawadzki, page 109–112 1981.*

* cited by examiner

Primary Examiner—Jean F. Vollano
(74) Attorney, Agent, or Firm—John Lezdey & Assoc

(57) ABSTRACT

There is provided a process for preparing tetraalkyl ammonium halide utilizing a catalytic amount of acetonitrile in a reaction under pressure and at an elevated temperature of an alkyl halide and a trialkyl halide and in which tetrafluoroborate can be subsequently prepared.

15 Claims, No Drawings

PROCESS FOR PREPARING TETRAFLUOROBORATE SALT AND INTERMEDIATES THEREOF

FIELD OF THE INVENTION

The present invention relates to the preparation of tetraalkyl ammonium tetrafluoroborates and to the intermediates thereof. More particularly, there is provided a process for preparing tetraalkyl ammonium tetrafluoroborates from tetraalkyl ammonium halide salts.

BACKGROUND OF THE INVENTION

Tetraalkyl ammonium tetrafluoroborates are useful in non-aqueous capacitors.

Tetraalkyl ammonium halides preparation has been described in U.S. Pat. No. 3,965,178 to Morris et al and in Japanese Patent No. 2000212132 to Shimada et al., and by Hossain et al. in *J. of Bangladesh Acad. Of Sciences.* Vol. 22, No. 1, 39–44(1998) in an article entitled "Kinetics of The Menschutkin Reaction of Pyridine With Benzyl Bromide In Different Solvents".

The preparation of tetraalkyl ammonium halide salts by the Menschutkin reaction is as follows:

$$RX + R'_3N \rightarrow RR'_3NX$$

where X=I, Br, Cl

This reaction is usually run in various solvents both protic and aprotic. The reaction runs faster in aprotic solvents such as benzonitrile, acetonitrile, tolene, nitrobenzene, propionitrile, acetone, etc. The rate of reaction is RI>RBr>RCl for the alkyl halides. The more bulky or substituted the reactant, the slower the reaction runs. Methyl bromide reacts much faster than ethyl bromide, which is faster than 2-bromopropane. The same is true of the alky chlorides, which are slower to start with. Trimethyl amine reacts faster than triethyl amine with the alkyl halide due to steric effects. The same steric effects are true with the alkyl halides. One of the slowest reacting situations is the reaction of an alkyl chloride with a trialkyl amine such as triethyl amine. For example:

$$\text{Ethyl chloride} + Et_3N \rightarrow Et_4NCl$$

SUMMARY OF THE INVENTION

The present invention provides a method for the preparation of tetraalkyl ammonium halides by the use of a catalytic amount of acetonitrile under pressure and elevated temperatures, which can be used in a further process for preparing tetraalkyl ammonium tetrafluoroborates.

More particularly, tetraalkyl ammonium halides can be prepared under an increased reaction rate and high yield wherein in the same reaction vessel can be prepared tetraalkyl ammonium tetrafluoroborate in high yields and purity.

According to the process, the acetonitrile can be removed after the initial preparation of the tetraalkyl ammonium halides and recycled into subsequent reactors.

Alternatively, the tetraalkyl ammonium halides can be recovered for other uses and for subsequent reactions to prepare tetraalkyl ammonium tetrafluoroborates.

It is therefore an object of the invention to provide a novel process for preparing tetraalkyl ammonium halides in high yields.

It is another object to prepare tetraalkyl ammonium tetrafluoroborates.

It is yet another object to provide a continuous process for preparing tetraalkyl ammonium tetrafluoroborates utilizing tetraalkyl ammonium halides as intermediates.

These objects and advantages of the invention will be more clearly understood from a reading of the preferred embodiments and examples, which follow.

PREFERRED EMBODIMENTS OF THE INVENTION

According to one embodiment of the invention, there is prepared tetraalkyl ammonium halides of the formula:

$$RR'_3NX$$

wherein

R is an alkyl group of 1 to 18 carbon atoms,

R' is an alkyl group of 1 to 8 carbon atoms, and

X is chloro, bromo or iodo.

Preferably, R and R' are methyl, ethyl or propyl groups.

The tetraalkyl ammonium halides are prepared by reacting a trialkyl amine having 3 to 8 carbon atoms with at least a 20% stochiometric excess of an alkyl halide having up to 18 carbon atoms, preferably 1 to 8 carbon atoms in the presence of a catalytic amount of acetonitrile, preferably about 5 to 50% of the reaction mass at a temperature of about 70 to 180° C., preferably, about 100 to 150° C. at a pressure of about 80 to 200 psi, preferably, about 160 to 180 psi.

It has been found that the reaction rate and the subsequent yield was increased by the following means:

1. Use of at least 20% to 100% excess of the stoichiometric amount of alkyl halide.
2. Use of a catalytic amount of at least 5 to 50% by weight of the reaction mass of acetonitrile, preferably 20 to 40% by weight.

The tetraalkyl ammonium halide can be recovered after the removal of the volatile by conventional means and then dissolving the remaining solid product in water or methanol.

According to another embodiment of the invention, after removal of the volatiles, tetraalkyl ammonium tetrafluoroborate can be prepared by the addition of aqueous fluoroboric acid into the reaction mixture. The fluoroboric acid can be prepared in situ with hydrofluoric acid and boric acid.

The process has the advantage that there may be a continuous process whereby the acetonitrile excess is used in a subsequent reactor.

The preferred alkyl halides are methyl chloride, ethyl chloride and propyl chloride.

The preferred trialkyl amines are trimethyl amine, triethyl amine, alkyl dimethylamine, methyldiethyl amine and tripropyl amine.

It is further understood that the preparation of tetraalkyl ammonium tetrafluoroborate can be prepared using tetraalkyl ammonium halides prepared by prior art means.

The following examples are provided to show specific embodiments and are given for illustration purposes and not by way of limitation:

EXAMPLE 1

Preparation of Tetraethylammonium Chloride with Excess Alkyl Halide

Into a 1-liter SS (stainless steel) pressure bomb with a magnetic stirrer was charged 201 g. of triethyl amine, 85 g. acetonitrile (100 ml), and 180 g. ethyl chloride (37% excess). The bomb was sealed and the contents stirred while being heated to 140° C. The pressure reached 175 psi. The reaction was stirred 5.5 hours at temperature and then was cooled to room temperature. The bomb was vented and then the volatile contents removed under vacuum at 80–100° C. The yield of off white crystals of tetraethylammonium chloride was 325 g. (99% yield).

Comparative Example 1

Preparation of Tetraethylammonium Chloride with Excess Amine

Into a 1-liter SS pressure bomb with a magnetic stirrer was charged 300 g. (50% excess) of triethylamine, 85 g. acetonitrile (100 ml), and 130 g. ethyl chloride. The bomb was sealed and the contents stirred while being heated to 145° C. The pressure reached about 170 psi. The reaction was stirred 5.5 hours at temperature and then was cooled to room temperature. The bomb was vented and then the volatile contents removed under vacuum at 80–1000° C. The yield of off white crystals of tetraethylammonium chloride was 82 g. (25% yield).

EXAMPLE 2

Preparation of Tetraethylammonium Chloride with Excess Alkyl Halide and Less Acetonitrile Into a 1-liter SS pressure bomb with a magnetic stirrer was charged 201 g. of triethyl amine, 42 g. acetonitrile (50 ml), and 180 g. ethyl chloride (37% excess). The bomb was sealed and the contents stirred while being heated to 140° C. The pressure reached 175 psi. The reaction was stirred 10 hours and then was cooled to room temperature. The bomb was vented and then the volatile contents removed under vacuum at 80–100° C. The yield of off white crystals of tetraethylammonium chloride was 295 g. (90% yield).

EXAMPLE 3

Preparation of Tetraethylammonium Chloride with a Larger Amount of Acetonitrile

Into a 1-liter SS pressure bomb with a magnetic stirrer was charged 201 g. of triethyl amine, 160 g. acetonitrile (200 ml), and 180 g. ethyl chloride (37% excess). The bomb was sealed and the contents stirred while being heated at 140° C. The pressure reached 175 psi. The reaction was stirred 5.5 hours and then was cooled to room temperature. The bomb was vented and then the volatile contents were removed under vacuum at 80–100° C. The yield of off white crystals of tetraethylammonium chloride was 326 g. (99% yield).

Comparative Example 3

Preparation of Tetraethylammonium Chloride without Acetonitrile

Into a 1-liter SS pressure bomb with a magnetic stirrer was charged 201 g. of triethyl amine and 160 g. ethyl chloride (23% excess). The bomb was sealed and the contents stirred while being heated at 145° C. The pressure reached 175 psi. The was stirred 5.5 hours and then was cooled to room temperature. The bomb was vented and then the volatile contents removed under vacuum at 80–100° C. The off white crystals of tetraethylammonium chloride was 49 g. (15% yield).

EXAMPLE 4

Following the procedure of Example 3, the tetraalkyl ammonium chloride was prepared.

| Experiment | Triethyl Amine | Acetonitrile | Ethyl Chloride | % Yield |
| --- | --- | --- | --- | --- |
| 1 | 201 g | 85 g | 225 g (91% xs) | 90 |
| 2 | 201 g | 42 g | 130 g (no xs) | 39 |
| 3 | 201 g | 170 g | 80 g (MeCl) | 99 |

Comparative Example 4

Into a 1-liter SS pressure bomb with a magnetic stirrer was charged 300 g. (50% of triethyl amine, 85 g. acetonitrile (100 ml), and 130 g. methyl chloride (MeCl). The bomb was sealed and the contents stirred while being heated at 145° C. The pressure reached about 170 psi. The reaction was stirred 5.5 hours at temperature and then was cooled to room temperature. The bomb was vented and then the volatile contents removed under vacuum at 80–100° C. The yield of off white crystals of tetraethylammonium chloride was 82 g. (25% yield).

EXAMPLE 5

Conversion to the Tetrafluoroborate Salt

Into the SS bomb of Example 1 containing the crude methyltriethylammonium chloride were added 300 g water (endothermic dissolution) to form an aqueous solution of the methyltriethylammonium chloride. Then 132 g. (10% excess) boric acid, were added. To this slurry were added 275 g. 70% hydrofluoric acid (10% excess) with cooling to maintain the temperature below 30° C. The solution was then heated with vacuum to remove the water and hydrochloric acid, which formed. The evaporation and drying was continued under vacuum up to 100° C. and then cooled. The solid was then dissolved with an equal weight of hot methanol and transferred from the bomb to be recrystalized. The crude yield of methyltriethylammonium tetrafluoroborate was 99% (361 g.)

EXAMPLE 6

Preparation of methyltriethylammonium tetrafluoroborate

Into a 1-liter SS pressure bomb with a magnetic stirring bar was charged 201 g. triethyl amine, 200 ml acetonitrile, and the contents were cooled to 17° C. The solution was then saturated with methyl chloride, about 80 g. (needed 101 g. for theoretical). The bomb was closed and heated slowly up to 55° when the reaction became exothermic. The solution was strongly cooled and the temperature peaked at 119° C. with a pressure of 60 psi. The bomb was cooled and 41 g. additional methyl chloride was added. The solution was again heated up to 90° C. A mild exotherm carried the temperature to 93° C. and the reaction held at about 85° C. for 2.5 hours and then cooled. Pulled off all the volatiles to give a yield of the chloride of 299 g. (100%). Added 419 g. 48% fluoroboric acid and stirred for one hour at room temperature. Again pulled off all of the volatiles to give 400 g. of the product as damp solid. (About 98% yield).

EXAMPLE 7

Preparation of 1-propyltriethylammonium Tetrafluoroborate

Into a 1-liter SS pressure bomb with a magnetic stirring bar was charged 152 g. triehtyl amine, 176 ml acetonitrile, and 181 g. 1-propyl chloride. The bomb was closed and the contents heated at 140° C. for 5.5 hours. The bomb was cooled and vented. All of the volatiles were pulled off to give a yield of the chloride of 179 g. (100%). Added 243 g. 48% fluoroboric acid and stirred for one hour at room temperature. Again pulled off all of the volatiles at 100° C. to give about 210 g. crude product (96%).

From the above, it is apparent that many modifications and variations of the present invention are possible in light of the above teachings. It is therefore to be understood that within the scope of the appended claims, the invention may be practiced than as otherwise claimed.

What is claimed is:

1. A process for preparing tetraalkyl ammonium tetrafluoroborates which comprises the steps of:
   A. reacting a trialkyl amine with at least a 20% excess of an alkyl halide and in an amount of about 5 to 50% by weight of the reaction mixture at a temperature of about 70 to 180° C. and at a pressure of about 80 to 200 psi in a reactor to form tetraalkyl ammonium halide;
   B. removing any volatile components including acetonitrile, from said reactor, and then;
   C. reacting aqueous fluoroboric acid with the remaining contents of said reactor in step B in situ to form tetraalkyl ammonium tetrafluoroborate.

2. The process of claim 1 wherein said alkyl halide comprises up to 18 carbon atoms.

3. The process of claim 1 wherein said alkyl halide is selected from the group consisting of methyl chloride, ethyl chloride and propyl chloride.

4. The process of claim 1 wherein said trialkyl amine comprises 3 to 24 carbon atoms.

5. The process of claim 1 wherein said trialkyl amine is selected from the group consisting of trimethyl amine and triethylamine.

6. The process of claim 1 wherein the reaction in step B is at a pressure between 150 to 180 psi.

7. The process of claim 1 wherein said excess of alkyl halide is not greater than 100%.

8. The process of claim 1 wherein said acetonitrile removed in step B is recycled.

9. The process of claim 1 which is continuous.

10. A process for preparing tetraalkyl ammonium halide which comprises reacting a trialkyl amine having 3 to 24 carbon atoms with at least a 20% excess of an alkyl halide having up to 18 carbon atoms and acetonitrile in an amount of about 5 to 20% by weight of the reaction mass at a temperature of about 70 to 180° C. and a pressure up to about 80 to 200 psi in a reactor.

11. The process of claim 10 including the step of removing any volatiles and adding water to obtain an aqueous solution of said tetraalkyl ammonium halide.

12. The process of claim 10 wherein said alkyl halide is selected from the group consisting of methyl chloride, ethyl chloride and propyl chloride.

13. The process of claim 11 including the step of adding aqueous fluoroboric acid into said reaction to form tetraalkyl ammonium tetrafluoroborates in situ.

14. The process of claim 13 wherein said fluoroboric acid is formed in situ with boric acid and hydrofluoroboric acid.

15. The process of claim 1 in which the tetraalkyl ammonium halide is of the formula:

$$RR'_3NX$$

wherein R is an alkyl group of 1 to 18 carbon atoms, R' is an alkyl group of 1 to 8 carbon atoms, X is I, Br or Cl.

* * * * *

UNITED STATES PATENT AND TRADEMARK OFFICE
CERTIFICATE OF CORRECTION

PATENT NO. : 6,444,846 B1
DATED : September 3, 2002
INVENTOR(S) : Smith et al.

It is certified that error appears in the above-identified patent and that said Letters Patent is hereby corrected as shown below:

Title page,
Item [73], Assignee, should read -- Lithdyne International --

Column 5,
Line 14, should read -- an alkyl halide and acetonitrile in an amount of about 5 to 50% by --

Signed and Sealed this

Twenty-fourth Day of December, 2002

JAMES E. ROGAN
*Director of the United States Patent and Trademark Office*